United States Patent [19]

DeLuca, Jr. et al.

[11] 4,038,099

[45] July 26, 1977

[54] RUTILE-COATED MICA NACREOUS PIGMENTS AND PROCESS FOR THE PREPARATION THEREOF

[75] Inventors: Carmine V. DeLuca, Jr., Peekskill; Harold A. Miller, White Plains; George R. Waitkins, Croton-on-Hudson, all of N.Y.

[73] Assignee: The Mearl Corporation, Ossining, N.Y.

[21] Appl. No.: 176,335

[22] Filed: Aug. 30, 1971

[51] Int. Cl.² ............................................. C09C 1/00
[52] U.S. Cl. ................................... 106/291; 106/300; 106/308 B; 106/309
[58] Field of Search ................... 106/291, 300, 308 B, 106/309

[56] References Cited

U.S. PATENT DOCUMENTS

| | | | |
|---|---|---|---|
| 2,933,408 | 4/1960 | Dempster et al. | 106/308 B |
| 3,087,828 | 4/1963 | Linton | 106/291 |
| 3,331,699 | 7/1967 | Marshall | 106/291 |
| 3,861,946 | 1/1975 | DeLuca, Jr. et al. | 106/291 |

*Primary Examiner*—Winston A. Douglas
*Assistant Examiner*—J. V. Howard
*Attorney, Agent, or Firm*—Ostrolenk, Faber, Gerb & Soffen

[57] ABSTRACT

Nacreous pigment products comprising mica particles coated with translucent layers consisting essentially of titanium dioxide in the rutile form. A process for the preparation of such pigment products is disclosed, involving treatment with tin compounds, so that the $TiO_2$ coating will crystallize mainly in the rutile form rather than as anatase during calcination of the pigment. The rutile-coated mica exhibits markedly enhanced light stability as compared with anatase-coated mica pigment products.

10 Claims, No Drawings

RUTILE-COATED MICA NACREOUS PIGMENTS AND PROCESS FOR THE PREPARATION THEREOF

BACKGROUND OF THE INVENTION

1. Field of the Invention

This invention relates to nacreous pigments, and more particularly to pigments formed by the deposition of titanium dioxide coatings on mica particles, which exhibit nacreous, viz., "pearly" optical effects and which may also, depending upon the thickness of such coatings, additionally display iridescent effects, when viewed by reflected light.

2. The Prior Art

Nacreous pigments exhibit pearl-like and/or iridescent effects upon the transmission and reflection of light therethrough. As is well known in the art, the characteristics of such pigments depend upon optical interference phenomena as more fully described, for example, in "The Properties of Nacreous Pigments", Greenstein and Miller, Technical Papers, Volume XIII, Annual Technical Conference, Society of Plastic Engineers, May 1967.

Nacreous pigments are conventionally formulated for use in suspensions of light-transmitting resinous media which may be applied by dipping or spraying operations to form plastic coatings or by extruding, molding, casting or like techniques to provide solid plastic articles incorporating such pigments. Nacreous pigments so utilized should possess indexes of refraction which differ from the suspending media therefor since the pearly or nacreous effect displayed by such pigments depends upon the difference between the index of refraction of the oriented, plate-like pigment particles and the index of refraction of the medium in which such are dispersed.

Mica by itself is not a satisfactory macreous pigment inasmuch as such possesses an average index of refraction of about 1.58, a value which is far too low for good reflectivity in the conventional transparent resinous media, the average index of refraction of which is about 1.50. Excellent nacreous pigments may, however, be provided by the deposition of titanium dioxide coatings on mica flakes. Such pigments have been described, for example, in Quinn et al. U.S. Pat. No. 3,437,515, issued Apr. 8, 1969, and Rieger et al. U.S. Pat. No. 3,418,146, issued Dec. 24, 1968 and owned by the assignee of the present invention; and Linton U.S. Pat. No. 3,087,828, issued Apr. 30, 1963, and assigned to E.I. duPont Nemours and Company, Inc.

The titanium dioxide layers deposited on mica flakes in accordance with the techniques described in the above patents, or as otherwise heretofore proposed, have been in the anatase form. Titanium dioxide-coated mica nacreous pigments in which the titanium dioxide coatings consist essentially of rutile have not previously been known and could not, in fact, be prepared by the processes known in the art prior to the present invention.

It is among the objects of this invention to provide improved titanium dioxide-coated mica nacreous pigments, possessing particularly greater light stability than those titanium dioxide-coated mica pigments which could be prepared as previously described. An additional object of the invention is to provide such improved pigments which, by virtue of the fact that their $TiO_2$ layers are in the rutile form, also possess greater light reflectivity and higher chemical inertness than do those pigments with the $TiO_2$ in the in the anatace form. Yet a further object of the present invention is to provide a novel process for readily preparing such improved pigments in commercial quantities.

The nature and objects of the invention will be more fully apparent from consideration of the following detailed description thereof.

SUMMARY OF THE INVENTION

In accordance with the present invention it has been found that improved titanium dioxide-coated mica nacreous pigments may be provided wherein the titanium dioxide layers formed on the micaceous particles substrates consist essentially of rutile. It has been found that the rutile-coated nacreous pigment is markedly superior in light stability to anatase or anatase/rutile-coated mica pigments. The rutile-coated nacreous pigment also possesses improved optical reflectivity and chemical stability characteristics as compared with the latter pigments.

Furthermore, the rutile coating is achieved with nontoxic materials, and the products are therefore suitable for use in cosmetic applications.

The reflection properties of titanium dioxide-coated mica pigments may be determined from a form of the Fresnal Equation which defines the amount of light perpendicularly reflected by a thin film between two media of different refractive indexes:

$$R_{max} = \left( \frac{N_2^2 - N_1 N_3}{N_2^2 + N_1 N_3} \right)^2 \tag{1}$$

where $R_{max}$ is the reflectance, i.e., the percentage of the incident light which is reflected, at the wavelength of maximum reflection $N_2$ is the index of refraction of the thin film, and $N_1$ and $N_3$ are the refractive indexes of the media in front of and behind the film, respectively.

For $TiO_2$, a conventional supporting medium, and mica, $N_2$ is 2.75 for rutile or 2.53 for anatase, $N_1$ is 1.50 and $N_3$ is 1.58. Thus $R_{max}$ is 27.2% when the $TiO_2$ is rutile and only 21.2% when the $TiO_2$ is anatase. In point of fact both the rutile and anatase layers are somewhat porous, reducing their effective refractive indexes somewhat; the rutile layer, however, exhibits a greater relative reflectance irrespective of such porosity.

Titanium dioxide-coated mica and similar nacreous pigments may also exhibit interference colors upon the destructive interference and reinforcement of light because the $TiO_2$ is in the form of a thin film. This effect is a function of film thickness. For example, a reflection minimum occurs for perpendicularly incident light at wavelength λ for a film of refractive index N and thickness $t$ when $$Nt = (n-1)\lambda/2 \tag{2}$$

where $n$ is a small integer and $Nt$ is the optical thickness of the film. Similarly, a reflection maximum occurs where $$Nt = (2n-1)\lambda/4 \tag{3}$$

In accordance with the present invention, the rutile-coated mica nacreous pigments of the invention are prepared by additionally treating the mica particles to be coated with an acidic, tin compound-containing solution, such treatment facilitating the direct conversion of the amorphous titanium dioxide layer coated on such particles to the rutile form during the subsequent calcination of the pigment. The tin compound treatment may be carried out concurrently with the titanium dioxide deposition on the mica substrates. Alternatively, the mica flake particles to be coated are pre-treated with a tin compound-containing solution having a concentration, expressed as Sn, of from about 0.10 to 10% and the thus treated particles are thereafter coated with titanium dioxide in the amorphous form by deposition from a suitable titanium compound-containing coating bath. In accordance with the latter technique, the titanium dioxide-coated particles are subsequently removed from the coating bath and washed to remove excess acid and impurities therefrom, and then dried, and are finally calcined at temperatures in excess of about 650° C to convert the amorphous titanium dioxide to a coating consisting essentially of the desired rutile material on the mica particle supports.

The crystallization characteristics of titanium dioxide, upon calcining, differ quite markedly when such material is precipitated in the free form or deposited upon substrates other than mica, as compared with mica deposition. Thus, titanium dioxide precipitated in the free form crystallizes as rutile when calcined at temperatures of about 800° C or higher, regardless of whether the precipitation medium contains chloride, sulfate, or other ions. If free titanium dioxide is formed by the hydrolysis of $TiCl_4$, then the product produced by calcining at lower temperatures (even as low as 500° C or lower) will be in the rutile form. Free $TiO_2$ derived from an aqueous sulfate hydrolysis yields the anatase form when calcined at 600° C, but such is readily converted to rutile at higher temperatures, e.g., 700° to 800° or higher.

In marked contrast to the preceding phenomena, $TiO_2$ deposited on mica flake surfaces from a $TiCl_4$ coating system and calcined at 850° C still shows the anatase form of $TiO_2$. Similarly, titanium dioxide deposited on mica from a titanium sulfate aqueous solution and subsequently calcined at 900° C for as long as 72 hours is still in the anatase form. Thus, it appears that the mica substrate stabilizes the anatase crystal form and minimizes, if not prevents, the formation of rutile in the practice of prior art $TiO_2$ depositions.

Contrary to the above phenomena and, quite unexpectedly, we have found that strongly adherent, non-crazing and non-stripping rutile coatings on mica are produced when the mica particles are treated with an aqueous acidic tin compound-containing coating bath, and subsequently calcined. When, for example, the tin compound solution is employed in a pre-treatment prior to the $TiO_2$ deposition, calcining at temperatures of even as low as about 650° C converts the amorphous coating deposited to rutile in highly crystalline form, as demonstrated by X-ray diffraction powder pattern method.

The different crystal forms of $TiO_2$ to be expected under different formation conditions are indicated in Table I:

TABLE 1

| Calcin-ation Temp. | Crystal Forms of $TiO_2$ Precipitated and Treated in Different Ways | | | |
|---|---|---|---|---|
| | Free $TiO_2$ | | $TiO_2$* on Mica | |
| | From $TiOSO_4$ | From $TiCl_4$ | Without Tin | With Tin |
| 400° | Amorphous | Amorphous | Amorphous | Amorphous |
| 650° | Anatase | Rutile | Anatase | Rutile |
| 850° | Rutile | Rutile | Anatase | Rutile |

*$TiO_2$ from either $TiOSO_4$ or $TiCl_4$ sources.

The procedures of the prior art may under certain circumstances yield products of inferior qualtity which contain some rutile. This frequently results from the conversion of anatase which has been stripped from the mica substrate and, hence, lacks the stabilizing effect of the mica substrate on the anatase crystal structure. A product of this type is unsatisfactory because it is poor in nacreous luster; the $TiO_2$ which has been stripped scatters light in all directions instead of reflecting it directionally as suitably $TiO_2$-coated platelets do. In addition, portions of the mica flake surfaces which have been thus stripped do not contribute to the general reflectivity of the product, resulting in a lower net reflectivity per unit weight of the pigment.

The mechanism by which the tin compound treatment of the present invention facilitates the formation, upon calcination, of rutile coatings on mica substrates is not fully understood. One possibility is that the amorphous hydrated tin compound which deposits on the mica changes to cassiterite, the only crystal form of $SnO_2$, upon calcination, and since cassiterite is isomorphous with rutile it directs the crystallization of the subsequent $TiO_2$ during calcination to rutile.

In any case, the use of tin for present purposes is distinct from the use, for example, of tin or other compounds to form nucleating surfaces to facilitate the deposition of $TiO_2$ pigments on difficult to coat glass substrates (cf., Wein U.S. Pat. No. 2,871,139 granted Jan. 27, 1959, and Marshall et al. U.S. Pat. No. 3,331,699 granted July 18, 1967). Unlike the coating of glass substrates, the deposition of $TiO_2$ on mica substrates may readily be achieved by several techniques known in the art without the use of any tin compound treatment. We have, however, discovered in accordance with this invention, that the use of such a treatment insures the formation of substantially pure rutile coatings on mica particles in place of the normally obtained anatase coatings.

PREFERRED EMBODIMENTS OF THE INVENTION

The rutile-coated mica nacreous pigments of this invention are suitably formed on mica plates which pass through a 325-mesh screen and which vary from about 1 to 75 microns in length. Preferably, most of the mica platelets fall within 5–35 microns. They range from about 0.03 to 3.0 microns in thickness, the average platelet thickness being about 0.25 microns. On the average, the mica substrates have a specific surface area (measured by the BET method) of about 1.0 to 6.0 square meters per gram ($m^2/g$), preferably from about 2.0 to 4.5 $m^2/g$.

The $TiO_2$ layers formed upon such particles may, as will be recognized in the art, be formed with varying thicknesses, depending upon the desired optical characteristics of the pigment, viz., whether pearly or interference color effects are desired. Generally, the rutile layers may possess thicknesses varying from about 20 millimicrons to as much as 350 millimicrons. Within any given product, the rutile layers are substantially uniform in thickness.

As noted hereinabove, the rutile-coated mica pigments are prepared by treating the mica particles with an aqueous acidic solution of a suitable tin compound. For such purpose an aqueous solution of a variety of tin salts, whether in the stannic or stannous forms, may be so utilized. Materials which are useful include stannic sulfate, stannic chloride, stannic bromide, stannic fluoride, stannous chloride, stannous bromide, stannous fluoride, stannous iodide, and stannous sulfate. Mixed compounds can also be used as well as other tin compounds which can be readily rendered soluble in acidic solution, such as some tin salts of organic acids. It is also possible, although less convenient, to use metallic tin or tin oxide which may be dissolved to make the desired tin solution.

As specified hereinabove, both stannic and stannous compounds can be used, it being known that both types can hydrolyze. It is also known that solutions of stannous compounds are easily oxidized to the stannic state, so it is believed likely that the effective agent is some variety or form of stannic oxide or hydroxide, but confirming evidence for this has not been obtained. Stannic chloride is the preferred tin compound for use, as it is easily soluble in water and forms clear and stable solutions with only the addition of small amounts of a mineral acid.

The tin compound or mixture of such compounds is incorporated in the treating solution in concentrations within the range of 0.10 to 10%, preferably from 0.3 to 3.0%, expressed as Sn, thereof. A suitable mineral acid, e.g., hydrochloric acid, is also incorporated therein to solubilize the tin salts added to or formed in the solution. Generally, amounts of acid sufficient to maintain the acidity below 2.0 on the pH scale are employed in the mixture, a portion of such acid serving to inhibit the rapid hydrolysis of the tin compounds which otherwise would form turbid solutions.

When the mica particles are to be pre-treated with the tin compound-treating solution, they are suitably slurried in the solution at concentrations of from about 5 to 30%. After slurrying the particles in the solution for about 1 to 10 minutes at either ambient or elevated temperatures, they are removed, concentrated, and coated as described hereinafter. Alternatively, it may be preferred to carry out the tin compound treatment and the titanium dioxide deposition within the same bath. In such instance, the mica particles are slurried in a bath containing the hereinabove noted tin compound or compounds in the proportions specified, followed by addition of the materials described hereafter for effecting the titanium dioxide deposition.

It is also possible to coat the mica particles with amorphous $TiO_2$ without the use of tin, and then to treat the coated amorphous product with an aqueous solution of a tin compound. After calcining, the $TiO_2$ coating is found to be in the rutile form. Although such after-treatment is effective, it is less convenient.

The titanium compound coating bath should contain a suitable titanium compound which may be hydrolyzed to and deposits as a hydrous titaniun dioxide in the amorphous form on the mica particles. Such compound may, for example, comprise titanyl sulfate, titanium tetrachloride, or other soluble titanium compound or complex such as those described, for example, in the aforesaid Quinn et al. U.S. Pat. No. 3,437,515. Although a variety of coating systems can be used, the preferred one for simplicity and ease of operation is titanyl sulfate, with or without added $H_2SO_4$.

Suitably, the mica particles are slurried in the titanium compound-containing coating bath at concentrations within the range of from about 1 to 25%, while simultaneously maintaining the titanium compound concentration within the range of from about 0.5 to 7%, expressed as $TiO_2$. The system is heated to within the range of from about 60° to 110° C to effect hydrolysis of the titanium compound to hydrous titanium dioxide which is thereupon deposited in the amorphous form upon the surfaces of the mica particles. This process may require from as short a period as 10 minutes to as much as 4 hours to complete.

The thus coated mica particles are separated from the mother liquor by filtering, centrifuging, or settling operations, and thereafter washed with water to decrease their acidity and thus remove excess acid and impurities. Desirably, the isolated, coated mica is washed until it reaches a pH of at least about 2 and generally to a pH of about 3 or higher.

The amorphous titanium dioxide-coated mica filter cake may therafter be dried prior to carrying out the final, critical calcination operation. The drying may be effected in air at temperatures of from about 105° to 175° C, with drying periods of from 30 minutes up to 4 hours. The drying operation may be carried out under vacuum at temperatures of from about 20° to 110° C and under reduced pressure as low as 0.01 mm Hg, for periods of from 30 minutes up to as much as 20 hours. Alternatively, the drying step may be omitted.

Finally, the amorphous titanium dioxide-coated mica particles are calcined to convert the amorphous coating thereof to the desired rutile-coated mica pigments of this invention. As indicated hereinabove, substantially complete conversion of the titanium dioxide layers occurs when the calcination is carried out within the temperature range of from about 650° to 950° C for periods of from about 10 minutes to 3 hours or longer.

The following examples illustrate preferred embodiments of the rutile-coated mica nacreous pigments of the present invention and the process for the preparation thereof without, however, being intended as limiting thereof. In each example the first experiment involves the omission of the tin compound treatment of the invention, leading to an anatase on mica product, while the second experiment includes the use of the tin compound treatment leading to the improved rutile on mica product hereof.

EXAMPLE 1A

Control: $TiO_2$-Coating on Mica

Without Use of Tin Compounds 16.0 g. muscovite mica, characterized by a BET of 2.8 $m^2/g$, are weighed into a 250 ml. Erlenmeyer flask provided with a reflux condenser and a magnetic stirrer-hot plate. The mica is slurried in a solution consisting of 123 gm. of distilled water and 14.0 gm. of ammonium chloride. Then 126 gm. of filtered stock titanyl sulfate solution, containing the equivalent of 10.0% $TiO_2$ and 26% $H_2SO_4$, are added.

The slurry is brought to reflux in 30 minutes and held at reflux for 75 minutes. During the reaction period the mica acquires a series of reflection colors, ending at blue. After reflux, the hot slurry is filtered on a Buchner funnel. The filter cake is washed five times with 200 ml.

portions of distilled water, followed by 25 ml. of isopropanol. The filter cake is sucked dry with suction on the filter and then is placed in an oven for drying for 60 minutes at 110° C.

Finally, the product is calcined in a furnace for 60 minutes at 900° C. The final dry powder product shows a yellow-pearl reflection color, the amorphous, hydrated blue-reflecting coating having decreased in thickness during dehydration and crystallization. The X-ray diffraction powder pattern shows that this product consists of anatase on muscovite. Light stability tests show that a nitrocellulose film containing this product exposed in a standard Fade-Ometer test changes color after the first 60 hours, as will be described more fully below.

EXAMPLE 1B $TIO_2$-Coating on Mica with Use of

Tin Compound Pre-Treatment

This is the same procedure as Example 1A except for pre-treatment of the mica with a solution of a tin compound in the following way. 2.0 gm. of reagent grade $SnCl_4 \cdot 5H_2O$, 1.2 gm. of concentrated HCl, and distilled water to a total solution weight of 65 gm. are made up. To this are added 16.0 gm. of the same mica as used in Example 1A in a 100 ml. beaker, and the mixture heated with a magnetic stirring-hot plate to 55° C. The slurry is held at 55° C for 15 minutes and then filtered. The wet filter cake is used in place of the 16.0 gm. of mica of Example 1A, and the procedure of Example 1A is followed. After reflux, the mica has a red-gold reflection color. The eventual calcined product has a blue reflection color.

The X-ray diffraction powder pattern shows that this product consists of rutile on mucovite, in contrast to the product prepared in accordance with Example 1A in which the tin compound treatment of the mica is not used, which product consists of anatase on muscovite. In addition, the light stability test using the Fade-Ometer shows that the product of this example does not change in any way after 100 hours, in contrast to the product of Example 1A which changes in color after only 60 hours.

EXAMPLE 2A

Control: $TiO_2$-Coating on Mica Without

Use of Tin Compound

The procedure is similar to that of Example 1A and is as follows:

7.0 gm. of the same mica in a 250 ml. Erlenmeyer flask are slurried in a solution consisting of 64.8 gm. of the stock titanyl sulfate solution of Example 1A, 19.3 gm. of concentrated $H_2SO_4$, and 191.5 gm. of distilled water. The slurry is heated to reflux in 10 minutes, and held at reflux for 180 minutes, at which time the suspension displays a blue reflection color.

The slurry is filtered hot, and the filter cake is washed 10 times with 200 ml. portions of distilled water followed by drying at 110° C for 60 minutes and finally calcining for 60 minutes at 900° C. The final product has a red-orange reflection color.

The X-ray diffraction powder pattern shows the product to be anatase on muscovite. The light stability tests shows a color change after the first 60 hours.

EXAMPLE 2B $TiO_2$-Coating on Mica With Use of

Tin Compound Pre-Treatment

This procedure is similar to that of Example 2A, except for including the tin compound pre-treatment as follows:

7.0 gm. of the same mica are slurried for about one minute with 200 gm. of an aqueous solution at room temperature containing 2.0% $SnCl_4 \cdot 5H_2$ by weight and 1.2% concentrated hydrochloric acid by weight. The slurry is then filtered immediately, and the cake is added to a 250 ml. Erlenmeyer flask containing the same solution as in Example 2A.

After processing in the same way as in Example 2A, the final product shows a yellow-pearl reflection color.

The product of this example consists of rutile on muscovite, as shown by the X-ray diffraction powder method. The light stability test shows no change after 100 hours of exposure in the Fade-Ometer.

EXAMPLE 3A $TiO_2$-Coating on Mica Without

Use of Tin Compound

The procedure in this example is the same as that of Example 2A, except that 12.5 gm. of the same mica are used, rather than 7.0 gm. A red-gold reflection color is seen after 180 minutes of reflux of the coating bath slurry. The final calcined product shows a light gold reflection color.

This product consists of anatase on muscovite, and the light stability test shows a shift in reflection color to yellow-pearl after 80 hours of exposure in the Fade-Ometer.

EXAMPLE 3B $TiO_2$-Coating on Mica With Use of Tin Compound Pre-Treatment

The procedure of this example is the same as that of Example 2B, except that 12.5 gm. of the same mica are used instead of 7.0 gm. The tin compound pre-treatment is the same as that of Example 2B. A red-gold reflection color is seen after 180 minutes of reflux. The final calcined product shows a yellow-pearl reflection color.

The final product consists of rutile on muscovite. The light stability test shows no color change after 100 hours in the Fade-Ometer.

EXAMPLE 4A $TiO_2$-Coating on Mica Without Use of Tin Compound Pre-Treatment In this example a supply of mica different from that used in the previous examples is employed. The mica batch so utilized is characterized by a BET surface area of 3.0 $m^2$/gm. 16 gm. of this mica are placed in a 300 ml. round-bottom flask. The mica is slurried in 90 gm. of distilled water. The flask is fitted with a water-jacketed reflux condenser with a heating mantle placed on a magnetic stirrer. The system is heated up slowly, reaching 70° C after 50 minutes. At this point 81 gm. of the stock titanyl sulfate solution of Example 1A are added to the flask over a 5-minute period. The temperature drops to 56.5° C, and heating is resumed, reaching reflux in another 40 minutes. The slurry is held at reflux for 60 minutes at which point a yellow color can be observed. The slurry is then processed in the same way as in Example 2A, and the final product displays a yellow-pearl reflection appearance.

This product is anatase on muscovite, and the light stability test using the Fade-Ometer shows a color change to a bluish-pearl color after 60 hours of exposure.

EXAMPLE 4B

TiO$_2$-Coating on Mica With Use of

Tin Compound Pre-Treatment

The same procedure as used in Example 4A is followed, except that 1.8 gm. SnCl$_4$·5H$_2$O and 1.0 gm. concentrated HCl are added to the initial dispersion of mica in water. When 55° C is reached, the slurry is held at 55° C for 15 minutes, and then heating is resumed. At 70° C, the stock titanyl sulfate solution is added, as in Example 4A. The slurry is refluxed for 60 minutes and then procesed as in Example 4A. The final product has a blue reflection color.

This example yields a final product that is rutile coated on muscovite. The light stability test shows no color change of the product on exposure for 100 hours in the Fade-Ometer.

The well-known method of X-ray diffraction powder patterns may be employed to determine the type of crystal structure of the TiO$_2$, i.e., whether anatase or rutile. As is well known to those familiar with X-ray diffraction powder technique, the X-ray patterns obtained by the Debye-Scherrer method for TiO$_2$-coated mica show lines for muscovite mica as well as for anatase, rutile, or both. The various lines can be distinguished from each other, and anatase and rutile are readily identifiable.

The products of Examples 1A through 4B are presented in Table II, including the X-ray diffraction results. It is clearly evident that the rutile form is obtained in each experiment utilizing the tin compound treatment, and the parallel experiment in each case omitting the tin compound addition leads to the anatase form. Other variables do not affect the formation of the rutile as shown in the examples.

The standard Fade-Ometer test method employed in the respective examples for determining light stability involves the incorporation of the calcined product in a suitable lacquer for the preparation of a drawdown. A Bird Applicator is used, to form a coating of the dispersion on a black card of the Morest type. After drying the cards are exposed in the Fade-Ometer in 20-hour increments.

The pigment product is incorporated at 3.0% concentration in the drawdown lacquer having the following composition:

3.10% —15/20 sec. RS cellulose nitrate
6.7% —30/40 sec. RS cellulose nitrate
5.2% —Isopropyl Alcohol
3.0% —Butyl Carbitol
82.0% —n-Butyl Acetate The lacquer is chosen for the test work because films of cellulose derivatives are particularly sensitive to the effect of ultraviolet light in the presence of TiO$_2$-coated mica. The effects of light exposure are seen very rapidly in this simple nicrocellulose system.

The products of Examples 1A through 4B were so tested, and the results of the light stability tests in the Fade-Ometer are given in the preceding examples and summarized in Table II below. In every pair of experiments, that utilizing tin compound pre-treatment of the mica shows a significantly better light stability that that in which such a pre-treatment was not employed. The enhanced light stability thus correlates with the presence of the rutile form of the TiO$_2$ coating.

TABLE II

TiO$_2$- Coated Mica: Correlation of Improved Light Stability with Tin Compound Treatment of the Mica

| Ex. | Tin Treatment | TiO$_2$ From | Reflection Color-Light Stability | | |
|---|---|---|---|---|---|
| | | | Before | Time | After |
| 1A | None | Anatase | Yel. Pearl | 60 hr. | Blue Pearl |
| 1B | To 55°; filtered | Rutile | Blue | 100 | No change |
| 2A | None | Anatase | Red-Orange | 60 | Orange |
| 2B | RT; filtered | Rutile | Yel. Pearl | 100 | No change |
| 3A | None | Anatase | Lt. Gold | 80 | Yel. Pearl |
| 3B | RT; filtered | Rutile | Yel. Pearl | 100 | No change |
| 4A | None | Anatase | Yel. Pearl | 60 | Blue Pearl |
| 4B | to 55°; not filtered | Rutile | Blue | 100 | No change |

Notes:
RT - Room Temperature
Time - Exposure in the Fade-Ometer with observations at 20-hour increments.

It will be noted that the tin compound-treated, rutile pigments of Examples 1B–4B exhibit markedly enhanced light stability, notwithstanding the several variations as between the procedures employed in such experiments, e.g., with respect to the mica substrates, the coating solution compositions, the processing of the coating bath products, and the reflection colors exhibited by the respective pigments.

The calcined products differ in reflection color depending on titanium coating procedure, mica concentration and whether and how the tin compound is applied. The reflection color is a function of Nt. Thickness depends on the quantity of TiO$_2$ and tin compound (presumably SnO$_2$) deposited and the degree of porosity in the coating. Refractive index depends on composition and porosity. Thus, Nt varies with experimental procedure. To obtain a product with a specific reflection color, a specific procedure is kept constant except for variations in mica concentration. In this way the required mica concentration is determined.

The color sequence as Nt increases is: blue pearl, yellow pearl, light gold, gold, orange, red, purple, blue, green, yellow, red, etc. The effect of ultraviolet radiation on a nitrocellulose film containing TiO$_2$-coated mica is first a shift in reflection color in the direction of a smaller value of Nt followed by chalking of the film upon longer exposure. As previously mentioned, there is some porosity in the TiO$_2$ coating, this porosity consisting of voids or spaces between the tiny TiO$_2$ crystallites. It is likely that these voids are filled with nitrocellulose in the nitrocellulose drawdown. On exposure to ultraviolet energy, the TiO$_2$ can catalyze the oxidation of nitrocellulose. The effective refractive index of the TiO$_2$ layer apparently is reduced as the nitrocellulose is destroyed and replaced by air or other gases. As a consequence, Nt falls even though the thickness of the film is presumably unchanged, and the color change corresponds to a shift toward lower optical thickness.

The following further examples illustrate some of the specific applications of the products of this invention, and demonstrate various specific advantages accruing from the use of such products.

EXAMPLE 5

Polypropylene Step Chip of Rutile-Coated Mica Product

The blue product of rutile-coated mica, prepared in Example 4B, is incorporated in polypropylene and molded into a step chip as follows:

400 gm. of polypropylene molding powder are mixed and heated in a small Banbury Mill at 290° F. 5.0 gm. of the rutile-coated mica are added together with an additional 100 gm. of polypropylene molding powder, dispersion being effected with a total forward mixing time of 5 minutes. 30 lbs/in.$^2$ pressure is used on the ram, and the uniform mass is discharged from the mill. The material is granulated and then formed into the injection-molded test pieces, the step chips.

The step chips exhibit a lustrous blue appearance by reflected light. Examination of a step chip with a metallurgical microscope at magnifications of 500X and 1000X reveal essentially no stripping of the rutile coating from the surfaces of the mica platelets.

EXAMPLE 6

Simulated Pearls Coated with Pearl Rutile-Coated Mica Formulation

Simulated pearls are made by coating beads with the rutile-coated mica described in Example 3B, in accordance with the following technique:

1.50 gm. of the product of Example 3B are carefully dispersed in 98.5 gm. of a dipping lacquer of the following composition:

2.1% —15/20 sec. RS cellulose nitrate
4.6% —30/40 sec. RS cellulose nitrate
3.6% —Isopropanol
35.5% —Amyl acetate, high-boiling
54.2% —n-Butyl acetate White translucent glass beads, 8 mm. in diameter and with a single hold through the middle of each, are mounted on toothpicks and are dipped into the dipping lacquer dispersion to form four coatings thereon, allowing up to 2 hours for drying of the first coat and one-half hour for drying of the last coat.

The coated beads display the typical appearance of simulated pearls, and are comparable in quality and luster to those produced by dip coatings of lacquer suspensions of natural pearl essence and of basic lead carbonate, well known, high quality narcreous pigments. Thus, the rutile-coated mica can provide a high luster nacreous pigment product.

EXAMPLE 7

Lustrous Cream Eye Shadow Product

The blue reflection color product of Example 4B is incorporated in a compounded cream eye shadow base, using 3.0 gm. of the rutile coated mica and 17.0 of a cream eye shadow base, the latter of which consists of the following, by weight:

| Part A: | Stearic Acid | 16.0% |
|---|---|---|
| | Petrolatum | 25.0 |
| | Lanolin | 5.0 |
| Part B: | Propylene glycol | 5.0% |
| | Triethanolamine | 4.0 |
| | Methyl p-hydroxy-benzoate | 0.2 |
| | Water | 44.4 |
| Part C: | Perfume | 0.4% |

Part A and Part B are each heated to 70° C, and Part B is stirred into Part A. When the temperature falls to 40° C, with stirring, Part C is added.

When applied to the skin, this lustrous eye shadow product displays a lustrous effect, along with a blue highlight which tends to iridescence.

We claim:

1. A process for the preparation of a nacreous pigment, which comprises, in sequence:
   a. treating micaceous particles with an acidic, tin compound-containing solution having a concentration, expressed as Sn, of from 0.10 to 10% by weight;
   b. coating said particles with titanium dioxide in the amorphous form by deposition from a titanium compound-containing coating bath;
   c. removing the titanium dioxide-coated particles from the coating bath and washing said particles to remove excess acid and impurities therefrom; and
   d. calcining said particles at a temperature in excess of 650° C to produce the desired translucent coating consisting of titanium dioxide in the form of rutile thereon.

2. The process of claim 1, in which the micaceous particles are slurried in the tin compound-containing solution at concentrations of from 5 to 30% by weight.

3. The process of claim 1, in which the solution employed in step (a) contains a stannous or stannic sulfate or halide or a mixture of such compounds, and in which the reaction mixture is maintained during such step at acidities below pH 2.0 and at ambient or elevated temperature.

4. The process of claim 1, in which the micaceous particles are slurried in the coating bath of step (b) at concentrations of from 1 to 25% by weight and in which the titanium concentration in the bath is maintained within the range of from 0.5 to 7% by weight, expressed as $TiO_2$.

5. The process of claim 1, in which the titanium dioxide-coated particles are dried at temperatures within the range of from 20° to 175° C under reduced or atmospheric pressures, and are thereafter calcined in step (d) to produce the desired rutile coating at temperatures within the range of from 650° to 950° C.

6. A nacreous pigment, which consists essentially of micaceous particles having on the surfaces thereof, a translucent coating consisting of titanium dioxide in the form of rutile produced by the process of claim 1.

7. The pigment of claim 6, in which the micaceous particles are in the form of mica flakes whose major dimensions are from 1 to 75 microns and which have specific surface areas of from 1.0 to 6 square meters per gram, and in which the rutile coating has a thickness of from 20 to 350 millimicrons.

8. A nacreous composition, comprising a light-transmitting resinous medium having suspended therein or supported thereon the nacreous pigment of claim 6.

9. A process for the preparation of a nacreous pigment which comprises in sequence:
   a. treating micaceous particles with an aqueous, acidic solution containing a tin compound;
   b. coating said micaceous particles with titanium dioxide by deposition from a titanium compound containing coating bath;
   c. calcining said particles at an elevated temperature to produce a translucent coating of rutile form titanium dioxide on the micaceous particles.

10. A nacreous pigment, which consists essentially of micaceous particles having on the surface thereof, a translucent coating consisting of titanium dioxide in the form of rutile produced by the process of claim 9.

* * * * *